United States Patent [19]

Paret et al.

[11] 4,201,633
[45] May 6, 1980

[54] SEPARATING AROMATIC HYDROCARBONS FROM MIXTURES CONTAINING THEM

[75] Inventors: Giancarlo Paret; Alessandro Vetere, both of Milan; Giuseppe Iori, San Donato Milanese, all of Italy

[73] Assignee: Snamprogetti S.p.A., Milan, Italy

[21] Appl. No.: 904,270

[22] Filed: May 9, 1978

[30] Foreign Application Priority Data

May 12, 1977 [IT] Italy .................. 23474 A/77

[51] Int. Cl.² .................. B01D 3/40; C07C 7/08
[52] U.S. Cl. .................. 203/58; 203/60; 203/78; 585/805; 585/806; 585/808
[58] Field of Search .................. 203/58, 60, 57, 73, 203/78, 84, 91; 260/674 SE, 674 R, 674 N, 674 A; 548/317; 208/326

[56] References Cited

U.S. PATENT DOCUMENTS

| | | | |
|---|---|---|---|
| 2,840,511 | 6/1958 | Rylander et al. | 203/60 |
| 3,120,487 | 2/1964 | Norton et al. | 260/674 SE |
| 3,227,632 | 1/1966 | Schmalenbach et al. | 260/674 R |
| 3,434,936 | 3/1969 | Luther et al. | 260/674 SE |
| 3,980,528 | 9/1976 | Rescalli et al. | 203/58 |

*Primary Examiner*—Wilbur L. Bascomb, Jr.
*Attorney, Agent, or Firm*—Morgan, Finnegan, Pine, Foley & Lee

[57] ABSTRACT

A method for separating benzene, toluene, xylenes and higher aromatics from admixtures containing them is disclosed, said method being based on the use of a solvent which is a 5-atom cyclic derivative of urea in which at least one of the nitrogen atoms is bound to an alkyl.

Representative of this class of selective solvents is N,N'-dimethyl ethylene urea.

Procedure details and examples are given.

2 Claims, 1 Drawing Figure

SEPARATING AROMATIC HYDROCARBONS FROM MIXTURES CONTAINING THEM

The present invention relates to a method for the separation of aromatic hydrocarbons from mixtures which contain them. More particularly, this invention is related to a method for separating aromatic hydrocarbons by extractive distillation in the presence of an appropriate solvent. The term aromatic hydrocarbons is intended herein to indicate mixtures of benzene, toluene, xylenes and higher aromatics. A number of methods are known for the separation of aromatic hydrocarbons in which the extractive distillation is adopted.

Such methods, however, have a number of shortcomings, both inherent in the intricacy of the processing cycles which are used and, above all, in the properties of the solvents which are exploited.

The majority of the solvents which are known and used at present belong to the class of the high-boiling compounds, so that they, at the high temperatures which are required in a few points of the cycle run are prone to thermal decomposition phenomena.

In order that such phenomena may be offset somewhat, the addition of a cosolvent is generally adopted, and, in the majority of cases, the cosolvent is water.

As a matter of fact, water has the important and unique effect of making possible to lower the boiling point of such solvents, so that their thermal decomposition can be offset to a certain extent. Water, however, encourages the hydrolysis of a number of the solvents referred to above and hydrolysis products are formed, which have definitely poorer qualities than the pure solvents under the respect of the solvent power and are, in most cases, also corrosive.

Quite unexpectedly, it has been found that it is possible to carry out the separation of aromatic hydrocarbons from mixtures which contain them by adopting an extractive distillation run with an even nonaqueous solvent provided that the solvent which is used is selected from the group consisting of the 5-atom cyclic derivatives of urea having at least one of the nitrogen atoms bound to an alkyl radical.

Quite particular advantages are afforded, within the scope of the present invention, by the solvent called N,N'-dimethyl-ethylene urea, which can be used both as such and with a maximum contents of water of 5%.

In the following Table 1 a comparison of this solvent with other known solvent is displayed.

TABLE I

ACTIVITY COEFFICIENTS AT INFINITE DILUTION OF SATURATED HYDROCARBONS IN ANHYDROUS SOLVENTS AT 50° C.

| SOLVENTS | HYDROCARBONS | | |
|---|---|---|---|
| | n-hexane | n-heptane | n-octane |
| N,N'-dimethyl ethylene urea | 11.43 | 13.10 | 15.55 |
| N-methyl imidazole | 28.17 | 34.76 | 47.00 |
| Formylmorpholine | 28.74 | 39.69 | 47.51 |
| Sulpholane | 49.18 | 68.18 | 110.0 |

An object of the present invention is to provide a method for using N,N'-dimethyl-ethylene urea as an extraction solvent, in order to obtain, in a simple and cheap fashion the separation of the aromatic hydrocarbons from mixtures which contain them.

Figure 1:
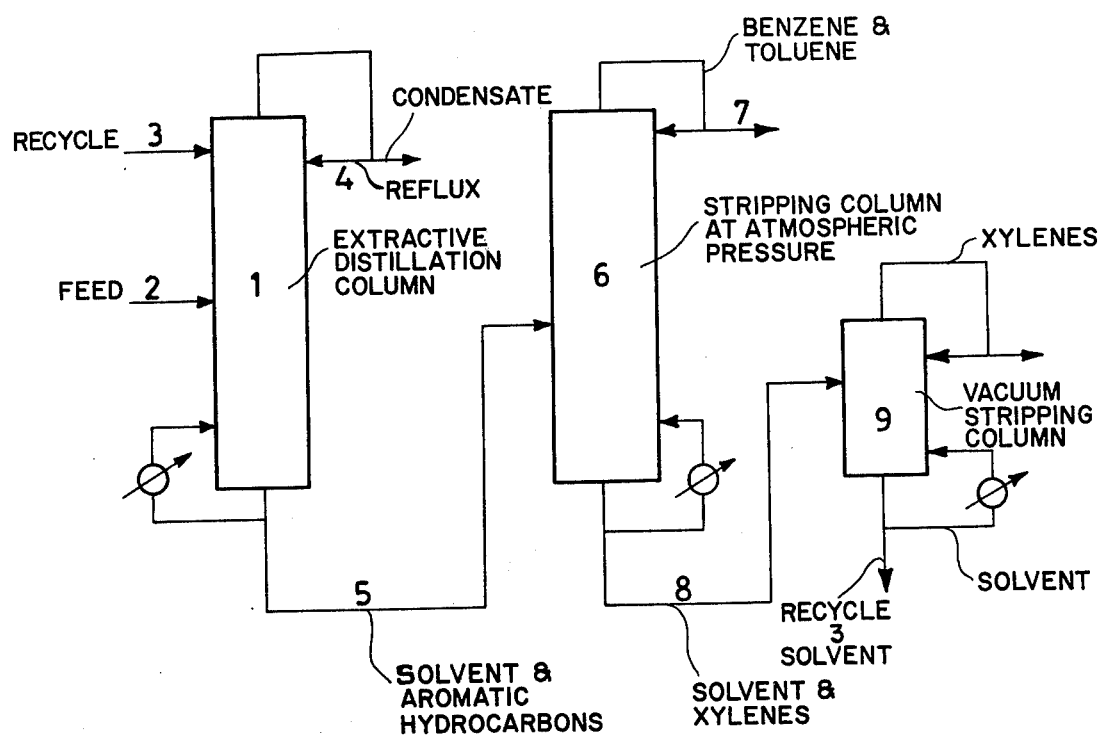
FIG. 1 is a flow chart that illustrates the process of the inventions.

The procedure which is preferred, according to the present invention, comprises the following steps:

(a) feeding the charge, which contains the aromatic hydrocarbons (benzene, toluene, xylenes and possibly higher homologs) to be separated, into the half-way section of an extractive distillation column, the solvent referred to above being fed in the vicinity of the column head.

(b) discharging from the head of the extractive distillation column a stream which is composed by nonaromatics and refluxing a portion of such a stream into the column, after having condensed said stream portion (c) discharging through the bottom of the extractive distillation column a stream which is composed by the solvent and the aromatic hydrocarbons (d) feeding the solvent and the aromatic hydrocarbons to a stripping column, under substantially atmospherical pressures, thus obtaining at the column head substantially all the benzene and toluene and a portion of the xylenes and, at the column tail the solvent with the remaining portion of the xylenes (e) feeding the solvent with the xylenes to a vacuum stripping column under a pressure of from 0.10 to 0.50 atm., preferably from 0.15 to 0.30 atm, the xylenes being separated at the head and the solvent at the tail, such solvent being recycled to the extractive distillation column.

It is important to note that the method according to this invention permits, inter alia, to have the two stripping columns operated at the same bottom temperature, so that considerable advantages are achieved as regards the entire processing run. It is likewise important to note that the two stripping stages are preferably performed with an external reflux to their heads in order that virtually solvent-free products may be recovered.

A few examples will now be given, which have the purpose of showing the thermal stability and the stability to hydrolysis as well, of N,N'-dimethyl-ethylene urea and of illustrating the invention without limiting it anyhow.

EXAMPLE 1

A sample of N,N'-dimethyl-ethylene urea has been placed in a stainless steel autoclave immersed in a melted salt bath kept at the temperature of 200° C. The samplings have been effected at 50-hour intervals for an overall duration of 700 hours. On completion of the tests no decomposition of the solvent has been ascertained, the sensitivity limit of the analysis methods being of 50 parts per million (ppm).

EXAMPLE 2

A sample of N,N'-dimethyl-ethylene urea which contained 5% by wt of water has been subjected to stability tests at the temperature of 180° C. in the apparatus of Example 1. After 700 hours the decomposition was 0.8 ppm an hour, as measured on the basis of the potentiometric titration of the dimethyl ethylene diamine as formed in the hydrolysis.

EXAMPLE 3

The test of Example 2 has been repeated at the temperature of 220° C. After 700 hours the decomposition was 1 ppm an hour.

As shown by examples 2 and 3, it is possible to use, if and when necessary, also mixtures of the solvent with water, the quantity of water being limited to a top value of 5% by wt, since no special advantages would be obtained with larger amounts of water.

EXAMPLE 4

Having now reference to the diagram of FIG. 1 of the accompanying drawings, the column 1 was fed via the line 2 with a stream composed by:

|  |  |
| --- | --- |
| Benzene | 15 parts |
| Toluene | 20 |
| Xylenes | 35 |
| Saturated hyd. | 30 |

The solvent, N,N'-dimethyl ethylene urea, was through the line 3 in an amount of 200 parts and contained 5.5 parts of xylenes. The column head gave the 30 parts of saturated hydrocarbons and 0.5 parts of xylenes. The reflux (line 4) was composed by 15 parts of saturated hydrocarbons and 0.25 parts of xylenes. The column bottom worked at 150° C. The bottom stream was composed by:

|  |  |
| --- | --- |
| Solvent | 200 parts |
| Benzene | 15 |
| Toluene | 20 |
| Xylenes | 40 | and was fed through the line 5 to the stripping column 6 so that at the head there were obtained through the line 7:

|  |  |
| --- | --- |
| Benzene | 15 parts |
| Toluene | 20 |
| Xylenes | 4.5 |

The stripping column 6 worked with a head reflux of 5.5 parts of aromatics and at a bottom temperature of 180° C., under atmospherical pressure.

The bottom product was fed through the line 8 to the vacuum stripping column 9 under a pressure of 0.2 atm, the bottom temperature being 190° C. The bottom stream of column 6 was composed by 200 parts of solvent and 35.5 parts of xylenes. The head stream of column 9 was composed by xylenes (30 parts) whereas the bottom stream was composed by the solvent (200 parts) and xylenes (5.5 parts), the solvent and the xylenes in question being recycled to the extractive distillation step 1 through the line 3.

We claim:

1. A method for the separation of aromatic hydrocarbons from mixtures containing them, comprising the steps of:
    (a) feeding the charge, which contains aromatic hydrocarbons, including benzene, toluene and xylenes to be separated, into the half-way section of an extractive distillation column, and a solvent compound of N,N$^1$-dimethyl ethylene urea into the upper area of the column,
    (b) discharging from the head of the extractive distillation column a stream which is composed of non-aromatics and refluxing a portion of such a stream into the column, after having condensed said stream portion,
    (c) discharging through the bottom of the extractive distillation column a stream which is composed of the solvent and the aromatic hydrocarbons,
    (d) feeding said solvent and the aromatic hydrocarbons to a stripping column, under substantially atmospheric pressures, thus obtaining at the column head substantially all the benzene and toluene and a portion of the xylenes and, at the column bottom the solvent with the remaining portion of the xylenes, and
    (e) feeding said solvent with the xylenes to a vacuum stripping column under a pressure of from 0.10 to 0.050 atm. the xylenes being separated at the head and the solvent at the bottom, such solvent being recycled to the extractive distillation column.

2. The method of claim 1 wherein the pressure is between 0.15 and 0.30 atmospheres.

* * * * *